US008454891B2

(12) United States Patent
Taesler

(10) Patent No.: US 8,454,891 B2
(45) Date of Patent: Jun. 4, 2013

(54) DISPOSABLE LABORATORY IMPLEMENT

(75) Inventor: Christian Taesler, Buxtehude (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 12/841,368

(22) Filed: Jul. 22, 2010

(65) Prior Publication Data

US 2010/0286382 A1 Nov. 11, 2010

Related U.S. Application Data

(63) Continuation of application No. 11/114,880, filed on Apr. 26, 2005, now abandoned.

(30) Foreign Application Priority Data

Aug. 17, 2004 (DE) .................... 20 2004 012 943 U

(51) Int. Cl.
*B01L 3/00* (2006.01)
*C07H 21/00* (2006.01)
*C07H 21/04* (2006.01)

(52) U.S. Cl.
USPC ........................................................ 422/50

(58) Field of Classification Search
USPC ........................................................ 422/102
See application file for complete search history.

(56) References Cited

U.S. PATENT DOCUMENTS

| | | | | |
|---|---|---|---|---|
| 6,303,233 | B1 * | 10/2001 | Amon et al. | 428/516 |
| 6,544,417 | B1 | 4/2003 | Tortorella | |
| 6,817,256 | B2 * | 11/2004 | Mehra et al. | 73/863.85 |
| 7,235,191 | B2 | 6/2007 | Schmidt et al. | |
| 7,473,463 | B2 * | 1/2009 | Wolfschwenger et al. | 428/216 |
| 2002/0109844 | A1 | 8/2002 | Christel et al. | |
| 2003/0219584 | A1 | 11/2003 | Higashi et al. | |
| 2006/0127282 | A1 * | 6/2006 | Yamashita et al. | 422/100 |

FOREIGN PATENT DOCUMENTS

| | | |
|---|---|---|
| EP | 1428854 A1 | 6/2004 |
| JP | 09077930 | 3/1997 |
| JP | 2002179860 | 6/2002 |
| JP | 2003-089734 | 3/2003 |
| WO | 9924479 | 5/1999 |

OTHER PUBLICATIONS

Machine Translation of Wada et al (JP2002-179860), 2002, 19 pages.*

Goto et al. JP2003089734. Proypylene Resin Composition. Translation May 2009. 25 pages.*

Okada et al. JP09-077930. Propylene Resin Composition Improved in High Speed Moldability and Transparency. Mar. 25, 1997, 13 pages.*

Goto et al.; "Polypropylene Resin Composition;" English Translation, May 2009.

Machine Translation of JP2002179860, Date of Translation: Mar. 18, 2008.

Machine Translation of JP09077930. Date of Translation: Mar. 18, 2008.

Gaillard, Claire, et al.; "Eliminating DNA loss and denaturation during storage in plastic microtubes;" Clinical Note; pp. 52-54; American Clinical Laboratory; Mar. 2001.

* cited by examiner

*Primary Examiner* — Christine T Mui
(74) *Attorney, Agent, or Firm* — Todd Lorenz; Arnold & Porter LLP

(57) ABSTRACT

A method of processing a liquid sample containing an initial quantity of nucleic acids that involves providing a plastic, disposable laboratory implement having at least one transparent wall segment made of a polypropylene mixed with an amount of a clarifier additive that is at least twice as high as is necessary to obtain transparency in the polypropylene, wherein the transparent wall segment exhibits a surface gloss greater than 160 as measured per DIN 67530 at an angle of 60°, bringing the liquid sample into contact with the at least one transparent wall segment and removing the liquid sample from the at least transparent wall segment, wherein the nucleic acid adsorption ratio for the transparent wall segment is less than 3 (wt/wt) relative to relative to the initial quantity of nucleic acids in the liquid sample.

8 Claims, No Drawings

DISPOSABLE LABORATORY IMPLEMENT

CROSS-REFERENCE TO RELATED APPLICATIONS

This application is a continuation of co-pending application Ser. No. 11/114,880, filed Apr. 26, 2005.

BACKGROUND OF INVENTION

1. Field of Invention

The present invention relates to a method of processing a liquid sample containing an initial quantity of nucleic acids using a single-use, hereinafter disposable, plastic laboratory implement.

2. Description of Related Art

In particular disposable implements of this kind are reaction receptacles, pipet tips and also microtitration plates. In general the present invention applies to all plastic implements used in the laboratory that may be applicable in processing liquid samples containing nucleic acids.

Disposable laboratory implements of this kind are made of polypropylene. It has been widely observed that nucleic acids interact with conventional polypropylenes in a manner that under some conditions the nucleic acids will bond for instance to the walls of the reaction receptacles.

The interaction between nucleic acids and different polypropylene reaction receptacles is described for instance in CLINICAL NOTES of March 2001, pp 52. This article cites a fact also observed by the applicant that conventional polypropylenes will bond nucleic acids especially at high salt concentrations. The processing of nucleic acids entailing various steps in the phase transition range, that is at high salt concentrations, the possibility of impoverishing the nucleic acids of interest when using conventional polypropylene implements cannot be excluded.

The publication above mentions that all tested conventional propylene receptacles exhibit substantially the same adsorption properties as regards nucleic acids. A few receptacles made with special materials exhibited less bonding for nucleic acids; however the source of this feature could not be ascertained for lack of manufacturer data.

U.S. Pat. No. 6,544,417 discloses making illustratively polypropylene laboratory implements by adding additives to them in a manner that the biomolecule's bonding ability shall be reduced. The additives described in U.S. Pat. No. 6,544,417 always are other plastics, for instance fluoropolymers such as TEFLON. Rigorously speaking, the compositions described therein are not plastics containing additives but blends or compounds of two different plastics. Contrary to additive containing plastics, the mixtures of materials known from the above U.S. patent do not permit making transparent laboratory implements.

BRIEF SUMMARY OF THE INVENTION

The objective of the present invention is to provide a method of processing a liquid sample containing an initial quantity of nucleic acids. The method involves providing a plastic, disposable laboratory implement having at least one transparent wall segment made of a polypropylene, which can be manufactured in an especially simple manner. The method of the present invention utilizes a laboratory implement that exhibits, in particular in the critical high salt range, a lower bonding affinity for nucleic acids than do conventional laboratory implements.

DETAILED DESCRIPTION OF THE INVENTION

Applicant surprisingly discovered that polypropylene surfaces exhibiting substantially higher surface gloss than standard polyproplyenes offer the lower bonding affinity to nucleic acids, especially under high salt conditions, which is sought in the present invention.

The expression "surface gloss" herein denotes the light reflecting property of surfaces. This surface gloss is defined as being the intensity of light reflected by a tested surface. Accordingly optically matte surfaces exhibit a value less than 10, medium glossy surfaces exhibit values between 10 and 70 and high-gloss surfaces values >70. Conventional polypropylenes exhibit a surface gloss of about 90.

The gloss values of the particular surface as a rule are measured at different angles of incidence (for instance 20, 60 or) 85°. Such measurements are carried out in internationally uniform manner according to DIN 67530 (Publication date: 1982-01), ISO 2813 (1994/Cor. 1997) or ASTM D523-89 (1999).

The values of the present invention all relate to measurements at 60°. The surface coefficient may be measured using commercially available apparatus. Illustratively MELIT Co. offers their "PicoGloss 560" which allows simple surface gloss measurements in the range which is significant for polypropylene.

Applicant presumes that, compared with conventional polypropylenes, those exhibiting the surface gloss of the invention exhibit fewer initial defects for instance in the form of edge roughness that, in the conventionally used polypropylenes may act as seed crystals and trigger the bonding of the nucleic acids to the walls of the disposable laboratory receptacles.

Polypropylenes exhibiting the surface gloss of the invention substantially differ from the conventional polypropylenes in that they show considerably smaller crystalline polypropylene units in the surface zones. This feature is attained using appropriate additives that will dissolve in the melt and upon solidification will precipitate as finely distributed seed crystals. The smaller the polypropylene units (the more crystallites available during solidification), the clearer the polypropylene shall be. Especially appropriate additives are the so-called clarifiers. A clarifier marketed under the name ADK STAB NA-21 for instance allows making polypropylenes exhibiting especially high surface gloss.

As discussed above, at least one wall zone making contact with the liquid sample is made from an additive-containing polypropylene where said additive introduces especially high gloss to a plastic surface which then evinces the desired reduced bonding affinity to nucleic acids at high salt conditions.

Within the scope of the invention basically all additives increasing polypropylene's surface gloss are applicable, but in especially preferred manner the said additive clarifier ADK STAB NA-21 offered by ADEKA PALMAROLA SAS (Strasbourg, France) will be used. This substance is aluminum hydroxybis[2,2'-methylenebis (4,6-di-tert-butylphenyl) phosphate]. Obviously other clarifiers and other additives allowing adjusting the surface gloss of the invention, such as the products MILLAD 3988, MILLAD 3950 and HPN-68 made by MILLIKAN Corp. or NC-4 made by MITSUI TOATSU Co. also are applicable. These products are diverse clarifiers generating the above discussed fine surface structure on the molded polypropylene part. Moreover additives such as polypropylene waxes may also be used to increase the surface gloss of polypropylenes.

To date, clarifiers have been added to plastics in the state of the art for the purpose of increasing implement transparency. The conventional concentrations of the above clarifier ADK Stab NA-21 are 0.09% (wt/wt) referred to the total weight. At such concentrations a slightly reduced bonding affinity of the polypropylene mixed with the clarifier already may be observed. However this slight effect is quite insufficient to process samples containing nucleic acids absent significant losses. The definite reduction in bonding affinity attained by the invention between polypropylene implements and nucleic acids will be sensible only when ADK STAB NA-21 is added to polypropylene in concentrations above 0.2% (wt/wt). Tests run by applicant show a minimum of 0.4% (wt/wt) of the said clarifier must be added to the polypropylene implements to keep the loss of nucleic acids during processing with the polypropylene implements at <1 (wt/wt) [relative to the initial quantity of nucleic acids]. Thus the clarifier concentrations selected in the invention to attain the desired bonding properties is much above the concentrations which are conventionally required for transparent plastic implements, the applicant having been first in discovering that, surprisingly, when adding unusually high clarifier concentrations, there results a dramatic change in the bonding behavior of polypropylene as compared to known transparent plastic implements.

The laboratory implements preferably may be pipet tips, syringes, vials storing liquid samples, microtitration plates, further bioarray slides, pestles or agitators etc. However the invention is not restricted to these implements. In principle those implements also are covered which, within the scope of processing liquid samples containing nucleic acids, will be in contact with the samples over an extended time interval.

According to the invention, at least the wall segments of the disposable laboratory implement that make contact with the liquid sample shall be made of a polypropylene mixed with an additive. Illustratively and in particular as regards microtitration plates, only the reaction receptacles (wells) need be made of polypropylene exhibiting the surface gloss of the invention whereas a frame supporting the reaction receptacles consists of another plastic, for instance a polycarbonate.

On the other hand, as regards other, more economical disposable laboratory implements, and in a preferred embodiment mode of the invention, the implements all are made from the additive-mixed polypropylene and as result all of them exhibit the surface gloss of the invention.

The invention is elucidated below in relation to several embodiment modes.

1. Measuring DNA Absorption as a Function of Gloss Coefficient.

Micro-reaction receptacles made by injection-molding polypropylenes fitted with various additives were used to measure the DNA adsorption at polypropylene surfaces by filling them with 50 μltr of a radioactively marked DNA solution (0.2 ng of DNA/μltr) at a 2.5 molar NaCl concentration and storing them in one test preparation for 24 h at 37° C. and in another test preparation for 10 min at 95° C. Then the solution was pipetted, that is completely evacuated. Next the reaction receptacle emptied in this manner was checked for its residual radioactivity. In this manner the DNA portion that was lost by adsorption in the reaction receptacle could be determined quantitatively.

It was found that reaction receptacles made of propylene to which the clarifiers ADK STAB NA-21, MILLAD 3988 and MILLAD 3950 exhibited considerably reduced DNA adsorption at the receptacle walls. Because the above additives increase the gloss of molded propylene surfaces—as determined on test bodies by the manufacturers of additives—the DNA adsorptivities may be correlated to the surface gloss and moreover a model may be developed (see above) to explain the adsorption differentials. The Table below shows numerical correlation values.

TABLE

DNA adsorption and gloss coefficient of polypropylenes with different additive treatments of polypropylene receptacles

| Material | DNA adsorption (37° C., 24 h) % wt/wt) | DNA adsorption (95° C., 10 min) (wt/wt) | Gloss coefficient at 60° [–]* |
|---|---|---|---|
| polypropylene no clarifier | 65-95 | >90 | 90 |
| polypropylene + 0.3% (wt/wt) MILLAD 3950 | 2.5 | 3.0 | 165 |
| polypropylene + 0.3% (wt/wt) MILLAD 3988 | 1.1 | 2.01 | 165 |
| polypropylene + 0.3% (wt/wt) ADK STAB NA-21 | 0.7 | 1.0 | 175 |

(*from Adeka Palmarole Deutschland GmbH)

2. Manufacturing a Disposable Laboratory Implement

The polypropylene receptacles are made by standard injection molding of polypropylene granulates. The corresponding additive, i.e. clarifier is either admixed using a master batch (a concentrate of the additive in polypropylene) as a granulate to the basic polypropylene granulate (that is, the two granulates are physically mixed as a dry blend and the mixture of granulates then is injection molded) or the additive shall already be contained from the beginning in the basic polypropylene granulate and is delivered from the manufacturer as the finished product. Furthermore the additive in the form of a pure substance may be admixed by using a compounding unit, for instance using a twin worm extruder, at the final desired proportion, into the polypropylene melt and to granulate the material from the melt after solidification. This granulate may then be injection molded.

What is claimed is:

1. A method of processing a liquid sample containing an initial quantity of nucleic acids, the method comprising:

bringing the liquid sample containing the initial quantity of nucleic acids into contact with a transparent wall segment of a disposable laboratory implement, wherein the transparent wall segment comprises a polypropylene and a clarifier at a concentration sufficient to introduce to the polypropylene a gloss coefficient of greater than 160 at an angle of 60° and a nucleic acid adsorptivity of less than 3% (wt/wt) of the initial quantity of nucleic acids in the liquid sample; and removing the liquid sample from the transparent wall segment of the disposable laboratory implement.

2. The method according to claim 1 wherein the gloss coefficient is greater than 170 at an angle of 60°.

3. The method according to claim 1, wherein the clarifier is aluminum hydroxybis[2,2'-methylenebis(4,6-di-tertbutylphenyl)phosphate].

4. The method according to claim 3, wherein the concentration of the aluminum hydroxybis[2,2'-methylenebis(4,6-di-tert-butylphenyl)phosphate] is greater than 0.2% (wt/wt) in the polypropylene.

5. The method according to claim 1, wherein the disposable laboratory implement is selected from the group consisting of a pipet tip, a reaction receptacle, a receptacle for storing liquid samples and a microtitration plate.

6. The method according to claim 1, wherein the disposable laboratory implement consists of polypropylene and the clarifier at a concentration sufficient to introduce to the polypropylene a gloss coefficient of greater than 160 at an angle of 60° and a nucleic acid adsorptivity of less than 3% (wt/wt) of the initial quantity of nucleic acids in the liquid sample.

7. The method according to claim 1, wherein the concentration of the clarifier is greater than 0.2% (wt/wt) of the total weight of the polypropylene and the clarifier.

8. The method according to claim 1, wherein the concentration of the clarifier is greater than 0.4% (wt/wt) of the total weight of the polypropylene and the clarifier.

* * * * *